(12) United States Patent
Gaffney et al.

(10) Patent No.: US 6,919,295 B2
(45) Date of Patent: Jul. 19, 2005

(54) SUPPORTED MIXED METAL OXIDE CATALYST

(75) Inventors: Anne Mae Gaffney, West Chester, PA (US); Scott Han, Lawrenceville, NJ (US); Michelle Doreen Heffner, Chalfont, PA (US); Nneka Namono McNeal, Carrollton, TX (US); Elsie Mae Vickery, Jenkintown, PA (US)

(73) Assignee: Rohm and Haas Company, Philadelphia, PA (US)

( * ) Notice: Subject to any disclaimer, the term of this patent is extended or adjusted under 35 U.S.C. 154(b) by 162 days.

(21) Appl. No.: 10/420,320

(22) Filed: Apr. 22, 2003

(65) Prior Publication Data

US 2003/0208085 A1 Nov. 6, 2003

Related U.S. Application Data

(60) Provisional application No. 60/376,769, filed on May 1, 2002.

(51) Int. Cl.[7] ................................................ B01J 23/00
(52) U.S. Cl. ......................... 502/311; 502/312; 558/323
(58) Field of Search ................................ 502/311, 312; 558/323

(56) References Cited

U.S. PATENT DOCUMENTS

| | | | |
|---|---|---|---|
| 5,281,745 A | 1/1994 | Ushikubo et al. | |
| 5,380,933 A | 1/1995 | Ushikubo et al. | |
| 6,043,185 A | 3/2000 | Cirjak et al. | |
| 6,063,728 A | 5/2000 | Hinago et al. | |
| 6,080,882 A | 6/2000 | Midorikawa et al. | |
| 6,194,610 B1 | 2/2001 | Borchert et al. | |

FOREIGN PATENT DOCUMENTS

| | | |
|---|---|---|
| EP | 0630879 B1 | 1/1998 |
| EP | 0962253 A2 | 12/1999 |
| EP | 1080784 A | 3/2001 |
| EP | 1312411 A | 5/2003 |
| EP | 1318127 A | 6/2003 |
| WO | WO 00/009260 | 2/2000 |
| WO | WO 00/029106 | 5/2000 |
| WO | WO 02/090308 | 11/2002 |

OTHER PUBLICATIONS

A. Cybulski and J.A. Moulijn (Eds.), "Structured Catalysts and Reactors", Marcel Dekker, Inc., 1998, pp. 599–615 (Ch 21 X. Xu and J.A. Moulijn, Transformation of a Structured Carrier into Structured Catalyst).
Abstract of Japanese Laid–Open Patent Application No. 6–228073(1994).
Abstract of Japanese Laid–Open Patent Application No. 7–53448 (1995).
Abstract of Japanese Laid–Open Patent Application No. 2000–37623(Feb. 8, 2000).

*Primary Examiner*—Kamal A. Saeed
(74) *Attorney, Agent, or Firm*—Marcella M. Bodner; Alan Holles

(57) ABSTRACT

A supported catalyst comprising a mixed metal oxide is useful for the vapor phase catalytic partial oxidation of an alkane, or a mixture of an alkane and an alkene, to an unsaturated carboxylic acid and for the vapor phase ammoxidation of an alkane, or a mixture of an alkane and an alkene, to an unsaturated nitrile.

8 Claims, No Drawings

SUPPORTED MIXED METAL OXIDE CATALYST

CROSS REFERENCE TO RELATED PATENT APPLICATION

This is a non-provisional application of prior pending U.S. provisional application Ser. No. 60/376,769 filed on May 1, 2002.

The present invention relates to an improved catalyst for the oxidation of alkanes or a mixture of alkanes and alkenes to their corresponding unsaturated carboxylic acids by vapor phase catalytic oxidation; to a method of making and supporting the catalyst; and to a process for the vapor phase catalytic oxidation of alkanes or a mixture of alkanes and alkenes to their corresponding unsaturated carboxylic acids. The present invention also relates to a method of producing unsaturated nitriles by subjecting alkanes or a mixture of alkanes and alkenes to vapor phase catalytic oxidation in the presence of ammonia.

Nitriles, such as acrylonitrile and methacrylonitrile, have been industrially produced as intermediates for the preparation of fibers, synthetic resins, synthetic rubbers, and the like. The most popular method for producing such nitriles is to subject an olefin, such as propene or isobutene, to a catalytic reaction with ammonia and oxygen, in the presence of a catalyst, in a gaseous phase at a high temperature. Known catalysts for conducting this reaction include a Mo—Bi—P—O catalyst, a V—Sb—O catalyst, an Sb—U—V—Ni—O catalyst, an Sb—Sn—O catalyst, a V—Sb—W—P—O catalyst and a catalyst obtained by mechanically mixing a V—Sb—W—O oxide and a Bi—Ce—Mo—W—O oxide. However, in view of the price difference between propane and propene, or between isobutane and isobutene, attention has been drawn to the development of a method for producing acrylonitrile or methacrylonitrile by an ammoxidation reaction wherein a lower alkane, such as propane or isobutane, is used as a starting material, and it is catalytically reacted with ammonia and oxygen in a gaseous phase in the presence of a catalyst.

In particular, U.S. Pat. No. 5,281,745 discloses a method for producing an unsaturated nitrile comprising subjecting an alkane and ammonia in the gaseous state to catalytic oxidation in the presence of a catalyst which satisfies the conditions:

(1) the mixed metal oxide catalyst is represented by the empirical formula

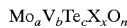

wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron and cerium, and, when a=1, b=0.01 to 1.0, c=0.01 to 1.0, x=0.01 to 1.0 and n is a number such that the total valency of the metal elements is satisfied; and (2) the catalyst has X-ray diffraction peaks at the following angles (±0.3°) of 2θ in its X-ray diffraction pattern: 22.1°, 28.2°, 36.2°, 45.2° and 50.0°.

Similarly, Japanese Laid-Open Patent Application Publication No. 6-228073 discloses a method of nitrile preparation comprising reacting an alkane in a gas phase contact reaction with ammonia in the presence of a mixed metal oxide catalyst of the formula

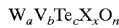

wherein X represents one or more elements selected from niobium, tantalum, titanium, aluminum, zirconium, chromium, manganese, iron, ruthenium, cobalt, rhodium, nickel, palladium, platinum, antimony, bismuth, indium and cerium, and, when a=1, b=0.01 to 1.0, c=0.01 to 1.0, x=0.01 to 1.0 and n is determined by the oxide form of the elements.

U.S. Pat. No. 6,043,185 also discloses a catalyst useful in the manufacture of acrylonitrile or methacrylonitrile by the catalytic reaction in the vapor phase of a paraffin selected from propane and isobutane with molecular oxygen and ammonia by catalytic contact of the reactants in a reaction zone with a catalyst, wherein the catalyst has the empirical formula

where X is one or more of As, Te, Se, Nb, Ta, W, Ti, Zr, Cr, Mn, Fe, Ru, Co, Rh, Ni, Pd, Pt, B, In, Ce, Re, Ir, Ge, Sn, Bi, Y, Pr, an alkali metal and an alkaline earth metal; an, when a=1, b=0.01 to 0.99, c=0.01 to 0.9, d=0.01 to 0.5, e=0.0 to 1.0 a determined by the oxidation state of the cations present.

Unsaturated carboxylic acids, such as acrylic acid and methacrylic acid, are industrially important as starting materials for various synthetic resins, coating materials and plasticizers. Commercially, the current process for acrylic acid manufacture involves a two-step catalytic oxidation reaction starting with a propene feed. In the first stage, propene is converted to acrolein over a modified bismuth molybdate catalyst. In the second stage, acrolein product from the first stage is converted to acrylic acid using a catalyst composed of mainly molybdenum and vanadium oxides. In most cases, the catalyst formulations are proprietary to the catalyst supplier, but the technology is well established. Moreover, there is an incentive to develop a single step process to prepare the unsaturated acid from its corresponding alkene. Therefore, the prior art describes cases where complex metal oxide catalysts are utilized for the preparation of unsaturated acid from a corresponding alkene in a single step.

European Published Patent Application No. 0 630 879 B1 discloses a process for producing an unsaturated aldehyde and a carboxylic acid which comprises subjecting propene, isobutene or tertiary butanol to gas phase catalytic oxidation with molecular oxygen in the presence of (i) a catalyst composite oxide represented by the formula

wherein A represents Ni and/or Co, B represents at least one element selected from Mn. Zn, Ca, Mg, Sn and Pb, C represents at least one element selected from P, B, As, Te, W, Sb and Si, and D represents at least one element selected from K, Rb, Cs and Tl, and wherein, when a=12,0<b≦10,0<c≦10, 1≦d≦10, 0≦e≦10, 0≦f≦20, 0≦g≦2 and x has a value dependent on the oxidation state of the other elements; and (ii) a molybdenum oxide which in itself is substantially inert to said gas phase catalytic oxidation to provide the corresponding unsaturated aldehyde and unsaturated carboxylic acid.

See also, European Published Patent Application No. 0 962 253 A2.

Japanese Laid-Open Patent Application Publication No. 07-053448 discloses the manufacture of acrylic acid by the gas-phase catalytic oxidation of propene in the presence of mixed metal oxides containing Mo, V, Te, O and X, wherein X is at least one of Nb, Ta, W, Ti, Al, Zr, Cr, Mn, Fe, Ru, Co, Rh, Ni, Pd, Pt, Sb, In, B, In, Li, Na, K, Rb, Cs and Ce.

Published International Application No. WO 00/09260 discloses a catalyst for selective oxidation of propene to acrylic acid and acrolein containing catalyst composition comprising the elements Mo, V, La, Pd, Nb and X in the following ratio:

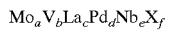

$Mo_aV_bLa_cPd_dNb_eX_f$ wherein X is Cu or Cr or a mixture thereof, a is 1, b is 0.01 to 0.9, c is >0 to 0.2, d is 0.0000001 to 0.2, e is 0 to 0.2, and f is 0 to 0.2; and wherein the numerical values of a, b, c, d, e and f represent the relative gram-atom ratios of the elements Mo, V, La, Pd, Nb and X, respectively, in the catalyst and the elements are present in combination with oxygen.

Commercial incentives also exist for producing acrylic acid using a lower cost propane feed. Therefore, the prior art describes cases wherein a mixed metal oxide catalyst is used to convert propane to acrylic acid in one step.

U.S. Pat. No. 5,380,933 discloses a method for producing an unsaturated carboxylic acid comprising subjecting an alkane to a vapor phase catalytic oxidation reaction in the presence of a catalyst containing a mixed metal oxide comprising, as essential components, Mo, V, Te, O and X, wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium; and wherein the proportions of the respective essential components, based on the total amount of the essential components, exclusive of oxygen, satisfy the following relationships: 0.25<r(Mo)<0.98, 0.003<r(V)<0.5, 0.003<r(Te)<0.5 and 0.003<r(X)<0.5, wherein r(Mo), r(V), r(Te) and r(X) are the molar fractions of Mo, V, Te and X, respectively, based on the total amount of the essential components, exclusive of oxygen.

Published International Application No. WO 00/29106 discloses a catalyst for selective oxidation of propane to oxygenated products including acrylic acid, acrolein and acetic acid, said catalyst system containing a catalyst composition comprising

$Mo_aV_bGa_cPd_dNb_eX_f$ wherein X is at least one element selected from La, Te, Ge, Zn, Si, In and W, a is 1, b is 0.01 to 0.9, c is >0 to 0.2, d is 0.0000001 to 0.2, e is >0 to 0.2, and f is 0 to 0.5; and wherein the numerical values of a, b, c, d, e and f represent the relative gram-atom ratios of the elements Mo, V, Ga, Pd, Nb and X, respectively, in the catalyst and the elements are present in combination with oxygen.

Japanese Laid-Open Patent Application Publication No. 2000-037623 discloses a method for producing an unsaturated carboxylic acid comprising subjecting an alkane to vapor phase catalytic oxidation in the presence of a catalyst having the empirical formula

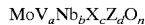

$MoV_aNb_bX_cZ_dO_n$ wherein X is at least one element selected from the group consisting of Te and Sb, Z is at least one element selected from the group consisting of W, Cr, Ta, Ti, Zr, Hf, Mn, Re, Fe, Ru, Co, Rh, Ni, Pd, Pt, Ag, Zn, B, Al, Ga, In, Ge, Sn, Pb, P, I, Y, rare earth elements and alkaline earth elements, $0.1 \leq a \leq 1.0$, $0.01 \leq b \leq 1.0$, $0.01 \leq c \leq 1.0$, $0 \leq d \leq 1.0$ and n is determined by the oxidation state of the other elements.

Despite the above-noted attempts to provide new and improved mixed metal oxide catalysts for the oxidation of alkanes to unsaturated carboxylic acids and for the ammoxidation of alkanes to unsaturated nitriles, and while the addition of a support material to the active catalyst can improve the physical properties of the catalyst, such as crush strength and reduced pressure-drop effects in the reactor, one impediment to the provision of a commercially viable process for such catalytic oxidations is the identification of a catalyst providing adequate conversion and suitable selectivity, thereby providing sufficient % yield of the unsaturated product.

By the present invention, there are provided catalysts wherein the performance is enhanced by supporting the catalyst in accordance with the principles herein. For instance, the catalyst is supported by: a self-supporting, multidimensional support structure that is pre-formed (e.g., a foam, a monolith, a fabric, or otherwise) and then contacted with the catalyst; a self-supporting, multidimensional support structure that is formed (e.g., extruded, cast or otherwise) from a composition comprising said catalyst; or a support (self-supporting or not) comprising precipitated and calcined alumina, $Nb_2O_5$, cordierite, partially stabilized zirconia (e.g., stabilized with MgO or CaO) or alumina/silica fiber. (As used herein, "self-supporting" in the context of a support structure means that the support structure will support its own weight sufficiently so that additional structure for carrying a catalyst may be avoided at the option of the operator.)

Accordingly, preferably the catalysts employed in the present invention are supported by a supporting technique selected from at least one of (i) contacting the catalyst with a pre-formed and self-supporting, multidimensional structure, (ii) forming a composition comprising the catalyst into a self-supporting, multidimensional structure, or (iii) admixing the catalyst with a support selected from precipitated and calcined alumina, $Nb_2O_5$, cordierite, partially stabilized zirconia or alumina/silica fiber.

Thus, in a first aspect, the present invention provides a catalyst comprising a mixed metal oxide having the empirical formula $Mo_aV_bE_cX_dO_e$, wherein E is at least one element selected from the group consisting of Te and Sb; X is at least one element selected from the group consisting of Nb, Ta, W, Ti, Al, Zr, Cr, Mn, Fe, Ru, Co, h, Ni, Pt, Bi, B, In, Ce, Se, As, Ge, Sn, Li, Na, K, Rb, Cs, Fr, Be, Mg, Ca, Sr, Ba, Hf, Ag, Pb, P, Pm, Eu, Gd, Dy, Ho, Er, Tm, Yb and Lu; and, when a=1, b=0.01 to 1.0, c=0.01 to 1.0, d=0.01 to 1.0 and e is dependent on the oxidation state of the other elements. Preferably, X is at least one element selected from the group consisting of Nb, Ta, W, Ti, Al, Zr, Cr, Mn, Fe, Ru, Co, Rh, Ni, Pt, Ag, Sb, I, B, In and Ce. Preferably, when a=1, b=0.1 to 0.5, c=0.05 to 0.5 and d=0.01 to 0.5; more preferably, when a=1, b=0.15 to 0.45, c=0.05 to 0.45 and d=0.01 to 0.1. The value of e, i.e. the amount of the oxygen present, is dependent on the oxidation state of the other elements in the catalyst. However, e is typically in the range of from 3 to 4.7.

The catalyst composition, before, during or after calcination (e.g., as discussed hereinafter) is combined with a support material. In one preferred aspect, the combination may be obtained by physically mixing (e.g., grinding with a mortar and pestle), impregnating or otherwise wetting, precipitating, co-precipitating, chemically depositing, vapor depositing, or the like, the mixed metal oxide material (or its precursors) for supporting contact with the desired support material. Preferred supports include precipitated and calcined alumina, $Nb_2O_5$, cordierite, partially stabilized zirconia (e.g., stabilized with MgO or CaO) and alumina/silica ceramic fiber. The support is mixed with the catalyst in a weight ratio of catalyst to support ranging from 0.1:99.9 to 20:80; preferably, from 0.5:99.5 to 15:85; and, more preferably, from 0.5:99.5 to 10:90. Particle size of the catalyst and support may typically range from 5 to 30 mesh and, more preferably, from 10 to 20 mesh (e.g., such as that resulting from 1 to 10 minutes of grinding with a mortar and pestle).

In another preferred aspect, the catalyst is formed into multi-dimensional form (e.g., a two- or three-dimensional form), with or without the above-described preferred supports, or is placed (e.g., coated or deposited) onto a multi-dimensional form, preferably for affording improved thermal stability, thermal integration and mass transfer along with pressure drop. The mixed metal oxide thus obtained may be used by itself as a solid catalyst in a multi-dimensional form, but may also be formed into a catalyst together with suitable multi-dimensional carrier.

More specifically the metal components of the presently contemplated catalyst may be supported on one or more suitable multi-dimensional structures, and preferably a ceramic support structure, e.g., that made of a material such as alumina, silica, silica-alumina, zirconia, titania, or the like. One technique useful for placing the catalyst components onto the support structure includes providing a support structure and then contacting the catalyst with the support structure by art-disclosed incipient wetness techniques. For example, in one typical method, solutions containing the metals are contacted with the three-dimensional structure (e.g., by impregnation, wash coating, slurry dip-coating, or otherwise wetting) such that the structure is wetted; then, the resultant wetted material is dried, for example, at a temperature from room temperature to 200° C. followed by calcination. In another method, metal solutions are contacted with the three dimensional structure, typically in volume ratios of greater than 3:1 (metal solution: three dimensional structure), and the solution is agitated such that the metal ions are ion-exchanged onto the three dimensional structure. The metal-containing three dimensional structure is then dried and calcined as detailed above.

In one particularly preferred aspect of the present invention, the ceramic support structure is an open or closed cell ceramic foam or monolith. More preferably, the ceramic is made from material selected from the group consisting of cordierite, alumina, zirconia, partially stabilized zirconia (PSZ), niobium and mixtures thereof. Of course, O other like materials may also be employed. The foam structure preferably has 30 to 150 pores per inch. The monoliths may have 200 to 800 cells per inch.

These forms for the support permit high space velocities with a relatively minimal pressure drop. The skilled artisan will be familiar with such configurations and the manner of making the same, in view of teachings such as "Structured Catalysts and Reactors, A. Cybulski and J. A. Moulijn (Eds.), Marcl Dekker, Inc., 1998, pp. 599–615 (Ch. 21 X. Xu and J. A. Moulijn, Transformation of a Structured Carrier into Structured Catalyst).

The catalyst components, with or without a ceramic support composition, may also be fabricated into a suitable two- or three-dimensional form or structure. For example, it is possible to extrude, cast or otherwise process the materials while in a flowable state to form a structure defining a suitable tortuous path, such as a honeycomb, foam or other suitable structure. Alternatively, the catalyst components may be fabricated into a reticulated foam or monolith structure to yield macroporous three-dimensional structures or monoliths which are generally self-supporting.

Structures including a fibrous or fabric support may also be employed. For instance, ceramic oxide fabric catalyst supports, fibrous ceramic composite catalysts, or a combination, provide other attractive supported structures, which are easily formed and are readily scaled to fit commercial reactors. These types of structures, which may or may not be self-supporting, preferably will resist thermal shock under the reaction conditions of interest and will generally avoid hot-spot induced circumstances, such as meltdown. These structures may be formed into any of a variety of three-dimensional configurations, and may employ one or more different fiber diameters, may be woven, unwoven or a mixture thereof, or even braided or otherwise aggregated into a suitable configuration, mesh or otherwise.

It will be appreciated as to the support structures disclosed herein that plural layers may be employed, with each layer having the same or different structure, composition, orientation, or other characteristic relative to a previous layer. For instance, a catalyst bed may contain a stack of layers of fabric discs formed from ceramic oxide fabric supported catalysts or the fibrous ceramic composite catalysts. Individual layers may or may not be self-supporting. Preferably, however, the combination embodied in the overall structure is generally self-supporting.

When employed herein, ceramic oxide fibers may be comprised of alumina, silica, boria, cordierite, magnesia, zirconia or a combination of any of these oxides. Loading of the catalyst precursor may be done using any suitable art-disclosed technique such as impregnation, wash coating, adsorption, ion exchange, precipitation, co-precipitation, deposition precipitation, sol-gel delivery, slurry dip-coating, microwave heating or the like. Alternatively, at least one refractory oxide, such as alumina, silica, boria, cordierite, magnesia or zirconia my be combined or mixed with the catalyst to form the active ceramic oxide fibers.

It will be appreciated that the supports of the present invention, though discussed above in the context of preferred groups of materials may be selected from any of a number of materials, such as (without limitation) a ceramic selected from the group consisting of cordierite, alumina, zirconia, partially stabilized zirconia (PSZ), niobium, silica, boria, magnesia, titania and mixtures thereof. The groups discussed herein are thus not intended as limiting.

In another aspect, multi-layer structures may include a stack of a plurality of perforated plates (e.g., thin, circular perforated metal discs), preferably joined together by a thermally conductive connection. The plates may be coated with an oxidation barrier, to thereby serve as a thermal shock resistant catalyst support for active catalyst materials. By way of illustration, recognizing that the teachings are applicable to other material systems or configurations, the catalyst preparation for this aspect includes fabricating a stack of thin, circular perforated metal discs and joining them together by a thermally conductive connection. The multi-disc structure is scaled at a high temperature for a sufficient time to grow an alumina layer. The multi-layer structure is impregnated with the active catalyst precursor material, dried and calcined. In one example, the multi-layer structure is scaled, or pretreated, by heating in air or oxygen at 900° C. to 1200° C., for a period of time ranging from about 10–100 hours, to form a thin, tightly adhering oxide surface layer which protects the underlying support alloy from further oxidation during high temperature use. The surface layer also preferably functions as a diffusion barrier to the supported metal catalyst, thus preventing alloying of the catalyst metal with the alloy of the catalyst support. For example, the protective surface layer may be composed predominantly of α-alumina, but also contains a small amount of yttrium oxide. After pretreatment, the multi-layer support structure is coated with a catalyst metal or catalyst precursor material. The coating may be achieved by any of a variety of methods known in the art, such as physical vapor deposition, chemical vapor deposition, electrolytic metal deposition, impregnation, deposition, wash coating or otherwise.

The supported catalysts as described herein may be further performance tuned as desired, and may be varied in their stacking, layering, or other integration characteristics in the reactor system in such a manner to improve reaction productivity. For example, in one aspect, it may be beneficial to initially provide an oxidative dehydrogenation active catalyst (supported as described herein or unsupported) upstream in the reactor system for the conversion of an alkane to alkene (e.g., propane to propylene) in the cases of pure, mixed and/or recycle streams. These forms might then be followed by supported or unsupported selective oxidation catalysts towards acid production.

Though other crystallographic results are possible, one preferred resulting supported catalyst according to the invention described herein exhibits the following five main diffraction peaks at specific diffraction angles 2θ in the X-ray diffraction pattern of the mixed metal oxide (as measured using Cu-Kα radiation as the source):

| | X-ray lattice plane | |
|---|---|---|
| Diffraction angle 2θ (±0.3°) | Spacing (Å) | Relative intensity |
| 22.1° | 4.02 | 100 |
| 28.2° | 3.16 | 20–150 |
| 36.2° | 2.48 | 5–60 |
| 45.2° | 2.00 | 2–40 |
| 50.0° | 1.82 | 2–40 |

The intensity of the X-ray diffraction peaks may vary upon the measuring of each crystal. However, the intensity, relative to the peak intensity at 22.1° being 100, is usually within the above ranges. Generally, the peak intensities at 2θ=22.1° and 28.2° are distinctly observed.

The present mixed metal oxide catalyst (or combination of catalyst and support) can be prepared in a suitable manner such as that illustrated in the following discussion. Thus, in a first step, a slurry or solution may be formed by admixing metal compounds, preferably at least one of which contains oxygen, and at least one solvent in appropriate amounts to form the slurry or solution. Preferably, a solution is formed at this stage of the catalyst preparation. Generally, the metal compounds contain elements Mo, V, E, X and O, as previously defined.

Suitable solvents include water; alcohols including, but not limited to, methanol, ethanol, propanol, and diols, etc.; as well as other polar solvents known in the art. Generally, water is preferred. The water is any water suitable for use in chemical syntheses including, without limitation, distilled water and de-ionized water. The amount of water present is preferably an amount sufficient to keep the elements substantially in solution long enough to avoid or minimize compositional and/or phase segregation during the preparation steps. Accordingly, the amount of water will vary according to the amounts and solubilities of the materials combined. However, as stated above, the amount of water is preferably sufficient to ensure an aqueous solution is formed, and not a slurry, at the time of mixing.

For example, when a mixed metal oxide of the formula $Mo_aV_bE_cX_dO_e$, wherein the element E is Te and the element X is Nb, is to be prepared, an aqueous solution of niobium oxalate may be added to an aqueous solution or slurry of ammonium heptamolybdate, ammonium metavanadate and telluric acid, so that the atomic ratio of the respective metal elements would be in the prescribed proportions.

Once the aqueous slurry or solution (preferably a solution) is formed, the water is removed by any suitable method, known in the art, to form a catalyst precursor. Such methods include, without limitation, vacuum drying, freeze drying, spray drying, rotary evaporation and air drying. Vacuum drying is generally performed at pressures ranging from 10 mmHg to 500 mmHg. Freeze drying typically entails freezing the slurry or solution, using, for instance, liquid nitrogen, and drying the frozen slurry or solution under vacuum. Spray drying is generally performed under an inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and at a pressure of from 10 mmHg to 760 mmHg, preferably at a bath temperature of from 40° C. to 90° C. and at a pressure of from 10 mmHg to 350 mmHg, more preferably at bath temperature of from 40° C. to 60° C. and at a pressure of from 10 mmHg to 40 mmHg. Air-drying may be effected at temperatures ranging from 25° C. to 90° C. Rotary evaporation or air-drying is preferred.

Once obtained, the catalyst precursor may be calcined into its desired supported form or into another suitable form. The calcination may be conducted in an oxygen-containing atmosphere or in the substantial absence of oxygen, e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 $hr^{-1}$.

The calcination is usually performed at a temperature of from 350° C. to 850° C., preferably from 400° C. to 700° C., more preferably from 500° C. to 640° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired mixed metal oxide.

In a preferred mode of operation, the catalyst precursor is calcined in two stages. In the first stage, the catalyst precursor is calcined in an oxidizing environment (e.g., air) at a temperature of from 275° C. to 400° C., preferably from 275° C. to 325° C. for from 15 minute 8 hours, preferably from 1 to 3 hours. In the second stage, the material from the first stage is calcined in a non-oxidizing environment (e.g., an inert atmosphere) at a temperature of from 500° C. to 700° C., preferably from 550° C. to 650° C., for from 15 minutes to 8 hours, for from 1 to 3 hours. Optionally, a reducing gas, such as, for example, ammonia or hydrogen, may be added during the second stage calcination.

In a particularly preferred mode of operation, the catalyst precursor in the first stage is placed in the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

Although any type of heating mechanism, e.g., a furnace, may be utilized during the calcination, it is preferred to conduct the calcination under a flow of the designated gaseous environment. Therefore, it is advantageous to conduct the calcination in a bed with continuous flow of the desired gas(es) through the bed of solid catalyst precursor particles.

With calcination, a catalyst is formed having the formula $Mo_a V_b E_c X_d O_e$ wherein E, X, a, b, c, d and e are as previously defined.

The starting materials for the above mixed metal oxide are not limited to those described above. A wide range of materials including, for example, oxides, nitrates, halides or oxyhalides, alkoxides, acetylacetonates, and organometallic compounds may be used. For example, ammonium heptamolybdate may be utilized for the source of molybdenum in the catalyst. However, compounds such as $MoO_3$, $MoO_2$, $MoCl_5$, $MoOCl_4$, $Mo(OC_2H_5)_5$, molybdenum acetylacetonate, phosphomolybdic acid and silicomolybdic acid may also be utilized instead of ammonium heptamolybdate. Similarly, ammonium metavanadate may be utilized for the source of vanadium in the catalyst. However, compounds such as $V_2O_5$, $V_2O_3$, $VOCl_3$, $VCl_4$, $VO(OC_2H_5)$, vanadium acetylacetonate and vanadyl acetylacetonate may also be utilized instead of ammonium metavanadate. The tellurium source may include telluric acid, $TeCl_4$, $Te(OC_2H_5)_5$, $Te(OCH(CH_3)_2)_4$ and $TeO_2$. The niobium source may include ammonium niobium oxalate, $Nb_2O_5$, $NbCl_5$, niobic acid or $Nb(OC_2H_5)_5$ as well as the more conventional niobium oxalate.

A mixed metal oxide, thus obtained, exhibits excellent catalytic activities by itself. However, the mixed metal oxide might also be converted to a catalyst having higher activities by grinding and then processing it into its desired supported form.

There is no particular restriction as to the grinding method, and conventional methods may be employed. As a dry grinding method, a method of using a gas stream grinder may, for example, be mentioned wherein coarse particles are permitted to collide with one another in a high-speed gas stream for grinding. The grinding may be conducted not only mechanically but also by using a mortar and pestle or the like in the case of a small-scale operation.

As a wet grinding method wherein grinding is conducted in a wet state by adding water or an organic solvent to the above mixed metal oxide, a conventional method of using a rotary cylinder-type medium mill or a medium-stirring type mill, may be mentioned. The rotary cylinder-type medium mill is a wet mill of the type wherein a container for the object to be ground is rotated, and it includes, for example, a ball mill and a rod mill. The medium-stirring type mill is a wet mill of the type wherein the object to be ground, contained in a container is stirred by a stirring apparatus, and it includes, for example, a rotary screw type mill and a rotary disc type mill.

The conditions for grinding may suitably be set to meet the nature of the above-mentioned promoted mixed metal oxide, the viscosity, the concentration, etc. of the solvent used in the case of wet grinding, or the optimum conditions of the grinding apparatus. However, it is preferred that grinding is conducted until the average particle size of the ground catalyst precursor would usually be at most 20 $\mu$m, more preferably at most 5 $\mu$m. Improvement in the catalytic performance may occur due to such grinding.

Further, in some cases, it is possible to further improve the catalytic activities by further adding a solvent to the ground catalyst precursor to form a solution or slurry, followed by drying again. There is no particular restriction as to the concentration of the solution or slurry, and it is usual to adjust the solution or slurry so that the total amount of the starting material compounds for the ground catalyst precursor is from 10 to 60 wt %. Then, this solution or slurry is dried by a method such as spray drying, freeze drying, evaporation to dryness or vacuum drying, preferably by the spray drying method. Further, similar drying may be conducted also in the case where grinding is conducted.

The oxide obtained by the above-mentioned method may be used as a final catalyst, but it may further be subjected to heat treatment usually at a temperature of from 200° C. to 700° C. for from 0.1 to 10 hour.

The present invention also provides a process for producing an unsaturated carboxylic acid, which comprises subjecting an alkane, or a mixture of an alkane and an alkene, to a vapor phase catalytic oxidation reaction in the presence of a supported catalyst containing the above mixed metal oxide, to produce an unsaturated carboxylic acid.

In the production of such an unsaturated carboxylic acid, it is preferred to employ a starting material gas that contains steam. In such a case, as a starting material gas to be supplied to the reaction system, a gas mixture comprising a steam-containing alkane, or a steam-containing mixture of an alkane and alkene, and an oxygen-containing gas, is usually used. However, the steam-containing alkane, or the steam-containing mixture of alkane and alkene, and the oxygen-containing gas may be alternately supplied to the reaction system. The steam to be employed may be present in the form of steam gas in the reaction system, and the manner of its introduction is not particularly limited.

Further, as a diluting gas, an inert gas such as nitrogen, argon or helium may be supplied. The molar ratio (alkane or mixture of alkane and alkene):(oxygen):(diluting gas):($H_2O$) in the starting material gas is preferably (1):(0.1 to 10):(0 to 20):(0.2 to 70), more preferably (1):(1 to 5.0):(0 to 10):(5 to 40).

When steam is supplied together with the alkane, or the mixture of alkane and alkene, as starting material gas, the selectivity for an unsaturated carboxylic acid is distinctly improved, and the unsaturated carboxylic acid can be obtained from the alkane, or mixture of alkane and alkene, in good yield simply by contacting in one stage. However, the conventional technique utilizes a diluting gas such as nitrogen, argon or helium for the purpose of diluting the starting material. As such a diluting gas, to adjust the space velocity, the oxygen partial pressure and the steam partial pressure, an inert gas such as nitrogen, argon or helium may be used together with steam.

As the starting material alkane it is preferred to employ a $C_{3-8}$ alkane, particularly propane, isobutane or n-butane; more preferably, propane or isobutane; most preferably, propane. According to the present invention, from such an alkane, an unsaturated carboxylic acid such as an ($\alpha,\beta$-unsaturated carboxylic acid can be obtained in good yield. For example, when propane or isobutane is used as the starting material alkane, acrylic acid or methacrylic acid will be obtained, respectively, in good yield.

In the present invention, as the starting material mixture of alkane and alkene, it is preferred to employ a mixture of $C_{3-8}$ alkane and $C_{3-8}$ alkene, particularly propane and propene, isobutane and isobutene or n-butane and n-butene. As the starting material mixture of alkane and alkene, propane and propene or isobutane and isobutene are more preferred. Most preferred is a mixture of propane and propene. According o the present invention, from such a mixture of an alkane and an alkene. An unsaturated carboxylic acid such as an ($\alpha,\beta$-unsaturated carboxylic acid can be obtained in good yield. For example, when propane and propene or isobutane and isobutene are used as the starting material mixture of alkane and alkene, acrylic acid or methacrylic acid will be obtained, respectively, in good yield. Preferably, in the mixture of alkane and alkene, the alkene is present in an amount of at least 0.5% by weight, more preferably, at least 1.0% by weight to 95% by weight, most preferably, 3% by weight to 90% by weight.

As an alternative, an alkanol, such as isobutanol, which will dehydrate under the reaction conditions to form its corresponding alkene, i.e. isobutene, may also be used as a feed to the present process or in conjunction with the previously mentioned feed streams.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethane, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane, It may be purchased, per se, or in admixture with an alkene and/or other impurities. Moreover, the alkane, regardless of source, and the alkene, regardless of source, may be blended as desired.

The detailed mechanism of the oxidation reaction of the present invention is not clearly understood, but the oxidation reaction is carried out by oxygen atoms present in the above mixed metal oxide or by molecular oxygen present in the feed gas. To incorporate molecular oxygen into the feed gas, such molecular oxygen may be pure oxygen gas. However, it is usually more economical to use an oxygen-containing gas such as air, since purity is not particularly required.

It is also possible to use only an alkane, or a mixture of alkane and alkene, substantially in the absence of molecular oxygen for the vapor phase catalytic reaction. In such a case, it is preferred to adopt a method wherein a part of the catalyst is appropriately withdrawn from the reaction zone from time to time, then sent to an oxidation regenerator. Regenerated and then returned to the reaction zone for reuse. As the regeneration method for the catalyst, a method may, for example, be mentioned which comprises contacting an oxidative gas such as oxygen , air or nitrogen monoxide with the catalyst in the regenerator usually at a temperature of from 300° C. to 600° C.

A process for producing an unsaturated carboxylic acid may also be employed where propane is used as the starting material alkane, and air is used as the oxygen source. In such an instance, the reaction system may be preferably a fixed bed system. The proportion of air to be supplied to the reaction system is important for the selectivity for the resulting acrylic acid, and it is usually at most 25 moles, preferably from 0.2 to 18 moles per mole of propane, whereby high selectivity for acrylic acid can be obtained. This reaction can be conducted usually under atmospheric pressure, but may be conducted under a slightly elevated pressure or slightly reduced pressure. With respect to other alkanes such as isobutane, or to mixtures of alkanes and alkenes such as propane and propene, the composition of the feed gas may be selected in accordance with the conditions for propane.

Typical reaction conditions for the oxidation of propane or isobutane to acrylic acid or methacrylic acid may be utilized in the practice of the present invention. The process may be practiced in a single pass mode (only fresh feed is fed to the reactor) or in a recycle mode (at least a portion of the reactor effluent is returned to the reactor). General conditions for the process of the present invention are as follows: the reaction temperature can vary from 200° C. to 700° C., but is usually in the range of from 200° C. to 550° C., more preferably 250° C. to 480° C., most preferably 300° C. to 430° C.; the gas space velocity, SV, in the vapor phase reaction is usually within a range of from 100 to 10,000 $hr^{-1}$, preferably 300 to 6,000 $hr^{-1}$, more preferably 300 to 3,000 $hr^{-1}$; the average contact time with the catalyst can be from 0.01 to 10 seconds or more, but is usually in the range of from 0.1 to 10 seconds, preferably from 0.2 to 6 seconds; the pressure in the reaction zone usually ranges from 0 to 75 pig, but is preferably no more than 50 psig. In a single pass mode process, it is preferred that the oxygen be supplied from an oxygen-containing gas such as air. The single pass mode process may also be practiced with oxygen addition. In the practice of the recycle mode process, oxygen gas by itself is the preferred source so as to avoid the build-up of inert gases in the reaction zone.

Of course, in the oxidation reaction of the present invention, it is important that the hydrocarbon and oxygen concentration in the feed gases be maintained at the appropriate levels to minimize or avoid entering a flammable regime within the reaction zone or especially at the outlet of the reactor zone. Generally, it is preferred that the outlet oxygen levels be low to both minimize after-burning and, particularly, in the recycle mode of operation, to minimize the amount of oxygen in the recycled gaseous effluent stream. In addition, operation of the reaction at a low temperature (below 450° C.) is extremely attractive because after-burning becomes less of a problem, which enables the attainment of higher selectivity to the desired products. The catalyst of the present invention operates more efficiently at the lower temperature range set forth above, significantly reducing the formation of acetic acid and carbon dioxides, and increasing selectivity to acrylic acid. As a diluting gas to adjust the space velocity and the oxygen partial pressure, an inert gas such as nitrogen, argon or helium may be employed.

When the oxidation reaction of propane, and especially the oxidation reaction of propane and propene, is conducted by the method of the present invention, carbon monoxide, carbon dioxide, acetic acid, etc. may be produced as by-products, in addition to acrylic acid. Further, in the method of the present invention, an unsaturated aldehyde may sometimes be formed depending upon the reaction conditions. For example, when propane is present in the starting material mixture, acrolein may be formed; and when isobutane is present in the starting material mixture, methacrolein may be formed. In such a case, such an unsaturated aldehyde can be converted to the desired unsaturated carboxylic acid by subjecting it again to the vapor phase catalytic oxidation with the mixed metal oxide-containing catalyst of the present invention or by subjecting it to a vapor phase catalytic oxidation reaction with a conventional oxidation reaction catalyst for an unsaturated aldehyde.

In yet another aspect, the method of the present invention comprises subjecting an alkane, or a mixture of an alkane and an alkene, to a vapor phase catalytic oxidation reaction with ammonia in the presence of a supported catalyst containing the above mixed metal oxide, to produce an unsaturated nitrile.

In the production of such an unsaturated nitrile, as the starting material alkane, it is preferred to employ a $C_{3-8}$ alkane such as propane, butane, isobutane, pentane, hexane or heptane. However, in view of the industrial application of nitrites to be produced, it is preferred to employ a lower alkane having 3 or 4 carbon atoms, particularly propane or isobutane.

Similarly, as the starting material mixture of alkane and alkene, it is preferred to employ a mixture of $C_{3-8}$ alkane and $C_{3-8}$ alkene such as propane and propene, butane and butene, isobutane and isobutene, pentane and pentene, hexane and hexene, or heptane and heptene. However, in view of the industrial application of nitriles to be produced, it is more preferred to employ a mixture of a lower alkane having 3 or 4 carbon atoms and a lower alkene having 3 or 4 carbon atoms, particularly propane and propene or isobutane and isobutene. Preferably, in the mixture of alkane and alkene, the alkene is present in an amount of at least 0.5% by weight, more preferably at least 1.0% by weight to 95% by weight, most preferably 3% by weight to 90% by weight.

The purity of the starting material alkane is not particularly limited, and an alkane containing a lower alkane such as methane or ethane, air or carbon dioxide, as impurities, may be used without any particular problem. Further, the starting material alkane may be mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the ammoxidation reaction of this aspect of the present invention is not clearly understood. However, the oxidation reaction is conducted by the oxygen atoms present in the above mixed metal oxide or by the molecular oxygen in the feed gas. When molecular oxygen is incorporated in the feed gas, the oxygen may be pure oxygen gas. However, since high purity is not required, it is usually economical to use an oxygen-containing gas such as air.

As the feed gas, it is possible to use a gas mixture comprising an alkane, or a mixture of an alkane and an alkene, ammonia and an oxygen-containing gas. However, a gas mixture comprising an alkane and an alkene and ammonia, and an oxygen-containing gas may be supplied alternately.

When the gas phase catalytic reaction is conducted using an alkane, or a mixture of an alkane and an alkene, and ammonia substantially free from molecular oxygen, as the feed gas, it is advisable to employ a method wherein a part of the catalyst is periodically withdrawn and sent to an oxidation regenerator for regeneration, and the regenerated catalyst is returned to the reaction zone. As a method for regenerating the catalyst, a method may be mentioned wherein an oxidizing gas such as oxygen, air or nitrogen monoxide is permitted to flow through the catalyst in the regenerator usually at a temperature of from 300° C. to 600° C.

A process may also be employed where propane is used as the starting material alkane, and air is used as the oxygen source. The proportion of air to be supplied for the reaction is important with respect to the selectivity for the resulting acrylonitrile. Namely, high selectivity for acrylonitrile is obtained when air is supplied within a range of at most 25 moles, particularly 1 to 15 moles, per mole of propane. The proportion of ammonia to be supplied for the reaction is preferably within a range of from 0.2 to 5 moles, particularly from 0.5 to 3 moles, per mole of propane. This reaction may usually be conducted under atmospheric pressure, but may be conducted under a slightly increased pressure or a slightly reduced pressure. With respect to other alkanes such as isobutane, or to mixtures of alkanes and alkenes such as propane and propene, the composition of the feed gas may be selected in accordance with the conditions for propane.

The process of the third aspect of the present invention may be conducted at a temperature of, for example, from 250° C. to 480° C. More preferably, the temperature is from 300° C. to 400° C. The gas space velocity, SV, in the gas phase reaction is usually within the range of from 100 to 10,000 $hr^{-1}$, preferably from 300 to 6,000 $hr^{-1}$, more preferably from 300 to 2,000 $hr^{-1}$. As a diluent gas, for adjusting the space velocity and the oxygen partial pressure, an inert gas such as nitrogen, argon or helium can be employed. When ammoxidation of propane is conducted by the method of the present invention, in addition to acrylonitrile, carbon monoxide, carbon dioxide, acetonitrile, hydrocyanic acid and acrolein may form as by-products.

The examples set forth below are for illustrative purposes only and should not be considered as limiting the scope of the invention. For purposes of this application, "% conversion" is equal to (moles of consumed alkane (or alkane/alkene)/moles of supplied alkane (or alkane/alene))×100; "% selectivity" is equal to (moles of formed desired unsaturated carboxylic acid or aldehyde/moles of consumed alkane (or alkane/alene))×100; and "% yield" is equal to (moles of formed desired unsaturated carboxylic acid or aldehyde/moles of supplied alkane (or alkane/alkene))× (carbon number of formed desired unsaturated carboxylic acid or aldehyde/carbon number of the supplied alkane (or alkane/alkene))×100.

EXAMPLES

Example 1

An Mo/V/Te/Nb mixed metal oxide was prepared in accordance with the techniques described in the present specification and used as the active catalyst ingredient. Alumina was formed by dissolving hydrous aluminum sulfate ($Al_2(SO_4)_3 \cdot 18H_2O$) in water and precipitating the hydrous oxide by addition of aqueous $NH_4OH$. The solid was filtered, washed with water, separated and calcined in air under a range of temperatures (600–900° C.). The alumina support was then physically mixed with the mixed metal oxide catalyst and tested for propane oxidation. For comparison purposes, zirconia and titania supports were prepared analogously to the alumina above (starting materials were zirconyl chloride ($ZrOCl_2$) and titanyl sulfate ($TiOSO_4 \cdot xH_2SO_4 \cdot xH_2O$)), mixed with the mixed metal oxide catalyst and tested for propane oxidation.

All catalysts were tested under conditions of 1 mole % propane mixed in air and passed through a saturator to give a water concentration of ~3%. Residence time was approximately 3 seconds. Reaction temperatures were from 350–380° C. with the result having the highest acrylic acid yield in that temperature range being reported. Products were analyzed by on-line Fourier Transform Infra-Red (FTIR) sampling. Final catalyst (mixture) surface areas and propane oxidation data are set forth in Table 1.

TABLE 1

| Catalyst Composition | Support Calcination Temp. (° C.) | Surface Area (m²/g) | Reaction Temp. (° C.) | $C_3H_8$ Conversion (mole %) | Acrylic Acid Yield (mole %) |
|---|---|---|---|---|---|
| MMO (1) | — | 5.1 | 350 | 35.7 | 20.6 |
| MMO + 0.5 wt % $Al_2O_3$ | 600 | 5.3 | 370 | 40.0 | 18.6 |
| MMO + 1.0 wt % $Al_2O_3$ | 600 | 5.8 | 380 | 44.1 | 18.9 |
| MMO + 5.0 wt % $Al_2O_3$ | 600 | 6.8 | 370 | 29.3 | 19.4 |
| MMO + 0.5 wt % $Al_2O_3$ | 700 | 7.3 | 370 | 39.7 | 18.2 |
| MMO + 1.0 wt % $Al_2O_3$ | 700 | 6.3 | 370 | 34.2 | 19.9 |
| MMO + 5.0 wt % $Al_2O_3$ | 700 | 8.3 | 350 | 37.7 | 23.0 |
| MMO + 0.5 wt % $Al_2O_3$ | 800 | 6.8 | 370 | 40.0 | 18.2 |
| MMO + 1.0 wt % $Al_2O_3$ | 800 | 6.9 | 370 | 34.0 | 18.7 |
| MMO + 5.0 wt % $Al_2O_3$ | 800 | 11.4 | 380 | 47.0 | 15.9 |
| MMO + 0.5 wt % $Al_2O_3$ | 900 | 6.5 | 370 | 38.2 | 17.4 |
| MMO + 1.0 wt % $Al_2O_3$ | 900 | 7.0 | 370 | 38.4 | 19.3 |
| MMO + 5.0 wt % $Al_2O_3$ | 900 | 10.2 | 380 | 44.8 | 16.1 |
| MMO + 0.5 wt % $TiO_2$ | 600 | 6.1 | 370 | 37.3 | 16.7 |
| MMO + 1.0 wt % $TiO_2$ | 600 | 6.0 | 350 | 42.0 | 16.8 |
| MMO + 5.0 wt % $TiO_2$ | 600 | 9.2 | 370 | 47.2 | 6.6 |
| MMO + 0.5 wt % $TiO_2$ | 700 | 7.0 | 370 | 46.5 | 17.3 |
| MMO + 1.0 wt % $TiO_2$ | 700 | 6.7 | 370 | 49.6 | 17.6 |
| MMO + 5.0 wt % $TiO_2$ | 700 | 8.0 | 370 | 43.7 | 7.7 |
| MMO + 0.5 wt % $TiO_2$ | 800 | 5.6 | 370 | 52.5 | 17.8 |
| MMO + 1.0 wt % $TiO_2$ | 800 | 6.2 | 370 | 49.4 | 16.6 |
| MMO + 5.0 wt % $TiO_2$ | 800 | 7.1 | 370 | 45.9 | 7.2 |
| MMO + 0.5 wt % $TiO_2$ | 900 | 5.2 | 380 | 48.5 | 18.1 |
| MMO + 1.0 wt % $TiO_2$ | 900 | 6.3 | 370 | 46.6 | 16.8 |
| MMO + 5.0 wt % $TiO_2$ | 900 | 6.5 | 380 | 48.0 | 13.7 |
| MMO + 0.5 wt % $ZrO^2$ | 600 | 5.9 | 370 | 31.5 | 14.3 |
| MMO + 1.0 wt % $ZrO^2$ | 600 | 6.0 | 370 | 37.5 | 20.0 |
| MMO + 5.0 wt % $ZrO^2$ | 600 | 8.9 | 350 | 26.7 | 3.0 |
| MMO + 0.5 wt % $ZrO^2$ | 700 | 6.3 | 370 | 33.6 | 19.2 |
| MMO + 1.0 wt % $ZrO^2$ | 700 | 6.5 | 370 | 57.2 | 19.1 |
| MMO + 5.0 wt % $ZrO^2$ | 700 | 6.8 | 350 | 29.6 | 7.4 |
| MMO + 0.5 wt % $ZrO^2$ | 800 | 6.5 | 380 | 47.3 | 11.5 |
| MMO + 1.0 wt % $ZrO^2$ | 800 | 7.8 | 370 | 42.3 | 6.2 |
| MMO + 5.0 wt % $ZrO^2$ | 800 | 16.4 | 380 | 46.8 | 1.2 |
| MMO + 0.5 wt % $ZrO^2$ | 900 | 5.5 | 380 | 47.8 | 18.6 |
| MMO + 1.0 wt % $ZrO^2$ | 900 | 6.0 | 370 | 44.5 | 18.3 |
| MMO + 5.0 wt % $ZrO^2$ | 900 | 6.7 | 350 | 26.6 | 16.4 |

(1) MMO = Mo/V/Te/Nb mixed metal oxide base catalyst.

The data in Table 1 indicate that alumina, prepared as indicated in Example 1, as the added support, exhibits the least deleterious effect, if any, on acrylic acid yield when tested under identical conditions to the zirconia- and titania-containing catalysts.

Example 2

In a flask containing 215 g of water, a three-component mixture of 25.68 g of ammonium heptamolybdate tetrahydrate (Aldrich Chemical Company), 5.06 g of ammonium metavanadate (Alfa-Aesar) and 7.68 g of telluric acid (Aldrich Chemical Company) were dissolved, heating to 70° C. After cooling to 40° C., 2.84 g of oxalic acid (Aldrich Chemical Company) were dissolved in 122.94 g of an aqueous solution of niobium oxalate (H. C. Starck), containing 1.25% Nb. This was then added to the three-component mixture to obtain a solution. The water of this solution was removed via a rotary evaporator with a warm water bath at 50° C. and 28 mmHg to obtain 46 g of precursor solid. Of this, 23 g of catalyst precursor solid were calcined in a quartz tube heated to 275° C. at 10° C./minute, with a 100 cc/minute flow of air through the tube, and held for one hour; then, using a 100 cc/minute flow of argon, ramped to 600° C. at 2° C./minute and held for 2 hours. The catalyst thus obtained was pressed in a mold and then broken and sieved to 10–20 mesh granules. Ten grams of the granules were packed into a 1.1 cm inside diameter stainless steel U-tube reactor for gas phase propane oxidation. The oxidation was conducted with a reactor bath (molten salt) temperature of 380° C., a 3 second residence time, a feed ratio of propane/air/steam of 1/15/14, and a space velocity of 1,200 $hr^{-1}$. The effluent from the reactor was condensed to separate the liquid phase (the condensable material) and the gas phase. The gas phase was analyzed by gas chromatography ("GC") to determine the propane conversion. The liquid phase was also analyzed by GC for the yield of acrylic acid. The results are shown in Table 2.

Example 3

The calcined mixed metal oxide of Example 1 was combined with $Nb_2O_5$ to give a mixture of 95% mixed metal oxide and 5% $Nb_2O_5$. Mixing was conducted in a mortar and pestle for 5 minutes. The ground mixture thus obtained was pressed in a mold and then broken and sieved to 10–20 mesh granules. Ten grams of the granules were packed into a 1.1 cm inside diameter stainless steel U-tube reactor for gas phase propane oxidation. The oxidation was conducted with a reactor bath (molten salt) temperature of 380° C., a 3 second residence time, a feed ratio of propane/air/steam of 1/1 5/14, and a space velocity of 1,200 $hr^{-1}$. The effluent from the reactor was condensed to separate the liquid phase (the condensable material) and the gas phase. The gas phase was analyzed by gas chromatography ("GC") to determine the propane conversion. The liquid phase was also analyzed by GC for the yield of acrylic acid. The results are shown in Table 2.

Example 4

The calcined mixed metal oxide of Example 1 was combined with cordierite to give a mixture of 95% mixed metal oxide and 5% cordierite. Mixing was conducted in a mortar and pestle for 5 minutes. The ground mixture thus obtained was pressed in a mold and then broken and sieved to 10–20 mesh granules. Ten grams of the granules were packed into a 1.1 cm inside diameter stainless steel U-tube reactor for gas phase propane oxidation. The oxidation was conducted with a reactor bath (molten salt) temperature of 380° C., a 3 second residence time, a feed ratio of propane/air/steam of 1/15/14, and a space velocity of 1,200 $hr^{-1}$. The effluent from the reactor was condensed to separate the liquid phase (the condensable material) and the gas phase. The gas phase was analyzed by gas chromatography ("GC")

to determine the propane conversion. The liquid phase was also analyzed by GC for the yield of acrylic acid. The results are shown in Table 2.

Example 5

The calcined mixed metal oxide of Example 1 was combined with partially stabilized zirconia to give a mixture of 95% mixed metal oxide and 5% partially stabilized zirconia. Mixing was conducted in a mortar and pestle for 5 minutes. The ground mixture thus obtained was pressed in a mold and then broken and sieved to 10–20 mesh granules. Ten grams of the granules were packed into a 1.1 cm inside diameter stainless steel U-tube reactor for gas phase propane oxidation. The oxidation was conducted with a reactor bath (molten salt) temperature of 380° C., a 3 second residence time, a feed ratio of propane/air/steam of 1/15/14, and a space velocity of 1,200 hr$^{-1}$. The effluent from the reactor was condensed to separate the liquid phase (the condensable material) and the gas phase. The gas phase was analyzed by gas chromatography ("GC") to determine the propane conversion. The liquid phase was also analyzed by GC for the yield of acrylic acid. The results are shown in Table 2.

Example 6

The calcined mixed metal oxide of Example 1 was combined with Nextel 610 (a ceramic fiber of 95% $Al_2O_3$ and 5% $SiO_2$, from 3M Company, Minneapolis, Minn.) to give a mixture of 95% mixed metal oxide and 5% Nextel 610. Mixing was conducted in a mortar and pestle for 5 minutes. The ground mixture thus obtained was pressed in a mold and then broken and sieved to 10–20 mesh granules. Ten grams of the granules were packed into a 1.1 cm inside diameter stainless steel U-tube reactor for gas phase propane oxidation. The oxidation was conducted with a reactor bath (molten salt) temperature of 380° C., a 3 second residence time, a feed ratio of propane/air/steam of 1/15/14, and a space velocity of 1,200 hr$^{-1}$. The effluent from the reactor was condensed to separate the liquid phase (the condensable material) and the gas phase. The gas phase was analyzed by gas chromatography ("GC") to determine the propane conversion. The liquid phase was also analyzed by GC for the yield of acrylic acid. The results are shown in Table 2.

TABLE 2

| Example | % Propane Conversion | % Acrylic Acid Yield |
|---|---|---|
| 2 | 17 | 12 |
| 3 | 33 | 21 |
| 4 | 27 | 19 |
| 5 | 34 | 21 |
| 6 | 35 | 22 |

Compared to the mixed oxide alone, the data in Table 2 indicate an increase in propane conversion and acrylic acid yield for mixtures of the mixed metal oxide with $Nb_2O_5$, cordierite, partially stabilized zirconia and $Al_2O_3/SiO_2$ ceramic fiber (Nextel 610). All of the supports alone ($Nb_2O_5$, cordierite, partially stabilized zirconia and $Al_2O_3/SiO_2$ ceramic fiber (Nextel 610)) were inactive in propane conversion.

Example 7

An amount of 12 mL of an aqueous solution containing ammonium heptamolybdate tetrahydrate (1.0M Mo), ammonium metavanadate (0.3M V) and telluric acid (0.23M Te), formed by dissolving the corresponding salts in water at 70° C., was added to a 50 mL Pyrex® tube. Then 6 mL of an aqueous solution of niobium oxalate (0.25M Nb) and oxalic acid (0.31M) were added thereto. After removing the water at 50° C., under 100 to 40 mmHg, the solid materials were further dried in a vacuum oven at 25° C. overnight and then calcined. (Calcination was effected by placing the solid materials in an air atmosphere and then heating them to 275° C. at 10° C./minute and holding them under the air atmosphere at 275° C. for one hour; the atmosphere was then changed to argon and the material was heated from 275° C. to 600° C. at 2° C./minute and the material was held under the argon atmosphere at 600° C. for two hours.)

The final catalyst (2.5 g) had a nominal composition of $Mo_1V_{0.3}Te_{0.23}Nb_{0.125}O_f$ and was ground to less than 325 mesh. 2.013 g of this powder was added to a vial along with 2.017 g of distilled water. The powder and distilled water were stirred in the vial to form a uniform slurry. An α-alumina, ceramic foam of 80 pores per square inch, 10 mm in length and 12 mm in diameter, acquired from Vesuvius High-Tech Company, was immersed into the slurry and completely wetted with the slurry. The coated foam was removed from the vial and the excess slurry was removed from the pores by blowing compressed air through the foam. The coated foam was dried in a vacuum oven at room temperature overnight after which time the weight loading of the mixed metal oxide was calculated. Five coated, (α-alumina, ceramic foams of the above dimensions were prepared by this method to give the respective wt % loadings of the mixed metal oxide of 30, 29, 26, 27 and 28. An uncoated control foam was also provided.

The five coated foams were stacked, one on top of another, and evaluated, for propane oxidation, simultaneously in a 45 cm long Pyrex® tube reactor with an internal diameter of 13 mm. The catalyst bed (50 mm long) was positioned with glass wool and ceramic tape at approximately mid-length in the reactor and was heated with an electric furnace. The void space above and below the bed was filled with ~3 mm α-alumina spheres. Mass flow controllers and meters regulated the gas flow rate. The oxidation was conducted using a feed gas stream of 7% propane, 14% oxygen, 27% steam and 52% nitrogen. The reactor effluent was analyzed by a gas chromatograph ("GC"). The results obtained at 410° C., with a residence time of 1.42 seconds, were 8.9% propane conversion, 16.3% oxygen conversion and 5.1% acrylic acid yield. The product selectivities were 56.9% acrylic acid, 32.8% propylene, 3.4% acetic acid, 3.4% $CO_2$, 2.7% CO, 0.5% propionic acid and 0.3% acetone. The uncoated foam saw no reaction.

While the invention has been described in conjunction with the specific embodiments set forth above, it is evident that many alternatives, modifications and variations will be apparent to those skilled in the art in light of the foregoing description. Accordingly, it is intended to embrace all such alterations, modifications and variations as fall within the spirit and scope of the appended claims.

What is claimed is:

1. A process for improving the performance characteristics of a catalyst, said process comprising:

a) providing precursors for a mixed metal oxide catalyst having the empirical formula

$$Mo_aV_bE_cX_dO_e$$

wherein E is at least one element selected from the group consisting of Te and Sb; X is at least one element selected from the group consisting of Nb, Ta, W, Ti, Al, Zr, Cr, Mn, Fe, Ru, Co, Rh, Ni, Pt, Bi, B, In, Ce, Se, As, Ge, Sn, Li, Na, K, Rb, Cs, Fr, Be, Mg, Ca, Sr, Ba, Hf, Ag, Pb, P, Pm, Eu, Gd, Dy, Ho, Er, Tm, Yb, Lu; and, when a=1, b=0.01 to 1.0, c=0.01 to 1.0, d=0.01 to 1.0 and e is dependent on the oxidation state of the other elements;

b) calcining an admixture of said precursors to form said mixed metal oxide catalyst; and c) forming said mixed metal oxide catalyst into a catalyst structure by at least one technique selected from the group consisting of (1) contacting said catalyst with a pre-formed and self-supporting, multidimensional structure, (2) forming a composition comprising said catalyst into a self-supporting, multidimensional structure and (3) admixing said catalyst with a support selected from the group consisting of alumina, $Nb_2O_5$, cordierite, partially stabilized zirconia and alumina/silica fiber.

2. The process of claim 1, wherein X is at least one element selected from the group consisting of Nb, Ta, W, Ti, Al, Zr, Cr, Mn, Fe, Ru, Co, Rh, Ni, Pt, Ag, Bi, B, In and Ce.

3. The process of claim 2, wherein, when a=1, b=0.1 to 0.5, c=0.005 to 0.5 and d=0.01 to 0.5.

4. The process of claim 1, wherein said pre-formed and self-supporting, multidimensional structure comprises a ceramic foam, a ceramic monolith or a ceramic fabric.

5. The process according to claim 1, wherein said pre-formed and self-supporting, multidimensional structure comprises a stack of a plurality of layers joined together by a thermally conductive connection.

6. The process according to claim 1, wherein said technique of (1) contacting said catalyst with a pre-formed and self-supporting, multidimensional structure comprises an incipient wetness technique.

7. The process according to claim 1, wherein said technique of (2) forming a composition comprising said catalyst into a self-supporting, multidimensional structure comprises forming a composition comprising said catalyst into a ceramic foam, a ceramic monolith or a ceramic fabric.

8. The process according to claim 1, wherein said technique of (3) admixing said catalyst with a support selected from the group consisting of alumina, $Nb_2O_5$, cordierite, partially stabilized zirconia and alumina/silica fiber comprises physically mixing, wetting, precipitating, co-precipitating, chemically depositing, vapor depositing or a combination thereof.

* * * * *